(12) United States Patent
Abdullah

(10) Patent No.: US 8,147,430 B2
(45) Date of Patent: Apr. 3, 2012

(54) APPARATUS AND METHOD FOR TESTING A HORSE'S TENDONS AND LIGAMENTS

(76) Inventor: Ahmad Ali Abdullah, Salmia (KW)

( * ) Notice: Subject to any disclaimer, the term of this patent is extended or adjusted under 35 U.S.C. 154(b) by 427 days.

(21) Appl. No.: 12/354,016

(22) Filed: Jan. 15, 2009

(65) Prior Publication Data

US 2010/0179450 A1    Jul. 15, 2010

(51) Int. Cl.
*A61B 5/117* (2006.01)
*A61B 5/103* (2006.01)

(52) U.S. Cl. ......................................... 600/592; 600/595

(58) Field of Classification Search .................. 600/587, 600/592, 595; 482/79, 131, 132, 127, 146, 482/147, 908; 601/27, 29, 32; 33/195, 471; 168/45; 702/43, 41; 156/73.1
See application file for complete search history.

(56) References Cited

U.S. PATENT DOCUMENTS

| | | | | |
|---|---|---|---|---|
| 4,733,859 A | * | 3/1988 | Kock et al. | 482/79 |
| 5,518,476 A | * | 5/1996 | McLeon | 482/79 |
| 5,897,464 A | * | 4/1999 | Mcleod | 482/79 |

\* cited by examiner

*Primary Examiner* — Brian Szmal
(74) *Attorney, Agent, or Firm* — Lowe Hauptman Ham & Berner, LLP

(57) ABSTRACT

An apparatus for testing a horse's tendons and ligaments includes a base plate and a rotatable plate with a guide member for receiving and positioning one of a horse's hooves thereon. A rod or lever is provided for manually rotating the rotatable plate up to and include an angle of 55° and a scale or indicator is provided for indicating the angle of rotation. A method for testing the horse's tendons and ligaments is also described.

12 Claims, 4 Drawing Sheets

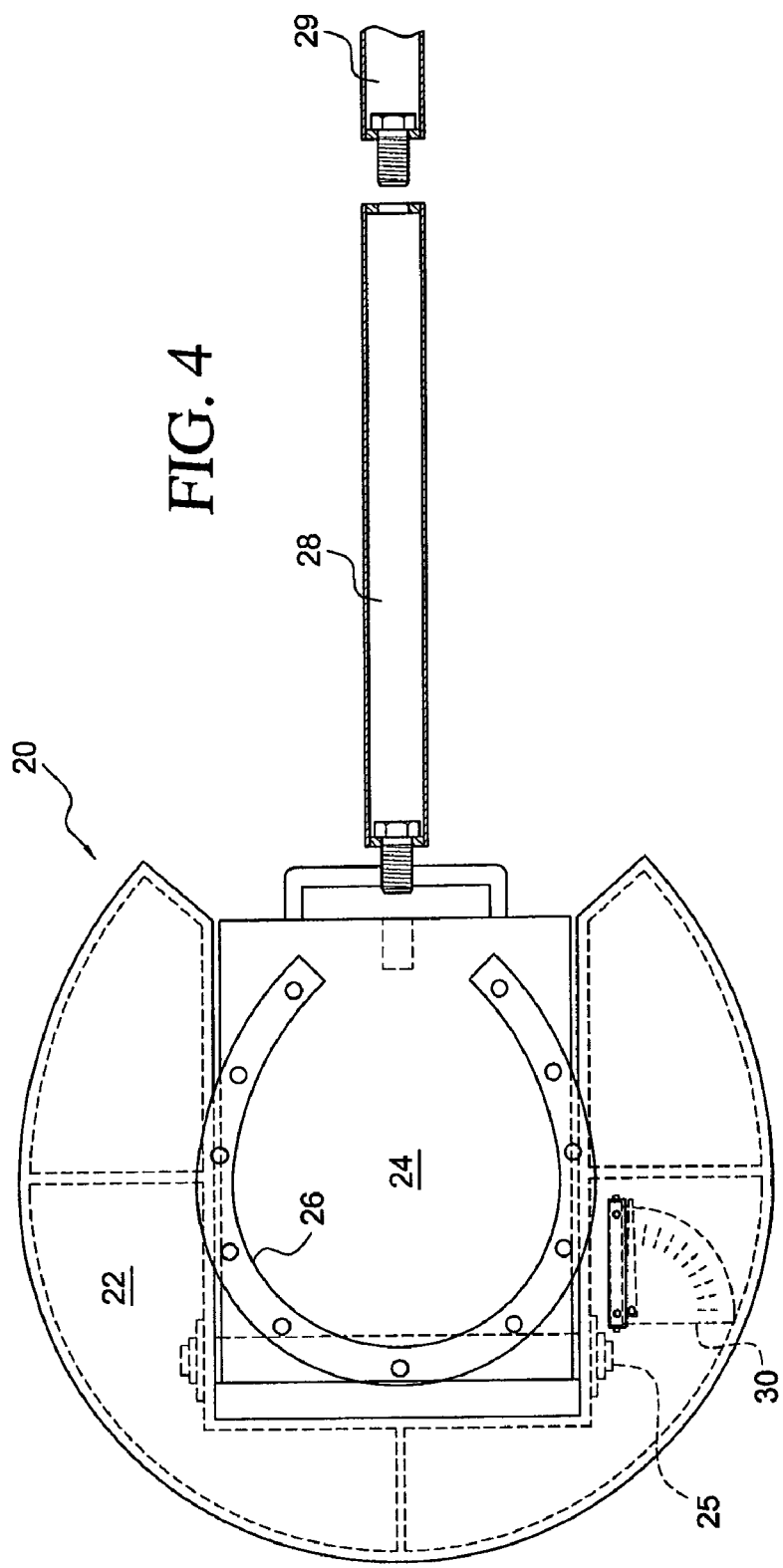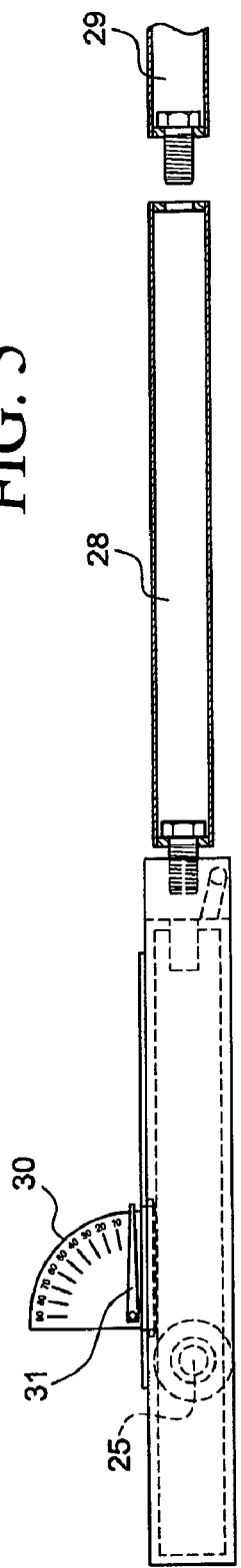

APPARATUS AND METHOD FOR TESTING A HORSE'S TENDONS AND LIGAMENTS

FIELD OF THE INVENTION

This invention relates to an apparatus and method for testing a horse's tendons and ligaments and more particularly to an apparatus and method for testing the soundness of a horse's tendons and ligaments by flexing a horse's lower leg.

BACKGROUND FOR THE INVENTION

Systems for measuring forces transmitted by a human or animal body both static and dynamic are well known. Such forces may be due to the motion of the body as for example locomotion of the body of humans and animals. Many of the early studies of such forces required a laboratory environment with force sensitive plates set into the floor or provided in a special platform. These plates were not easily portable.

A diagnostic force analysis system to measure time varying forces transmitted by a body is disclosed in a U.S. patent of Pratt, Jr. U.S. Pat. No. 4,195,643. As disclosed therein, the system can be used to measure physiological force associated with motion of the body such as the gait of humans or animals. A Fourier transform of a force balkistocardiogram and posture control forces were found to contain information to the physiological condition. The posture control forces can be used as a measure of lameness.

A more recent patent of Pourcelot et al., U.S. Pat. No. 7,010,435 discloses a Method for Measuring Tension State of Materials and Uses Thereof. The method includes the step of calculating the value of at least one perimeter extracted from an ultrasonic signal received after propagation of an ultrasonic source and at least an ultrasonic emitter located at a fixed distance from the source. The value of the at least one parameter varies with the state of tension of the material as for example a tendon or ligament.

Notwithstanding the above it is presently believed that there is a need for a portable apparatus for testing the soundness of a horse's tendons and ligaments in the horse's lower leg. There should be a demand for such apparatus in accordance with the present invention because it enables a relatively unskilled individual to test the soundness without the help of a veterinarian or technician, to perform the test where the horse is located and to quickly determine whether or not the horse's tendons and ligaments in the lower leg are sound or if the horse has suffered an injury to it's lower leg. Further, the apparatus according to the present invention is durable, relatively inexpensive and adapted to test different horses without making adjustments to the apparatus.

BRIEF SUMMARY OF THE INVENTION

In essence, the invention contemplates an apparatus for testing the soundness of a horse's tendons and ligaments by flexing a horse's lower leg. The apparatus includes a base plate having a forward and rear portion along a longitudinal axis and wherein the base plate is adapted to be placed on the ground underneath a horse's hoof. The apparatus also includes a rotatable plate that is rotatably fixed to the base plate and rotatable through an angle of at lease about 55° with respect to the base plate. A horseshoe shaped element for receiving and positioning a horse's hoof is provided on the rotatable plate with a forward portion of the horse's hoof with the forward or rear portion of the horse's hoof relatively close to a forward edge of the rotatable plate. In addition, the apparatus includes a lever fixed to a rear portion of the rotatable plate for manually tilting the rotating plate with a horse's hoof thereon and to rotate the plate to an angle of 55°. Finally, the apparatus includes an arc shaped scale for indicating the angle between the base plate and the rotatable plate as an indication of the soundness of a horse's tendons and ligaments in the horse's lower legs.

The present invention also contemplates a method for testing the soundness of a horse's tendons and ligaments by flexing a horse's lower leg. The method includes the step of providing an apparatus with a base plate and a rotatable plate that is adapted to be rotated with respect to the base plate to an angle of up to 55°. The method also includes the step of positioning a horse's hoof on the rotatable plate with the horse standing in a balanced position on four legs. The horse's hoof is elevated by manually rotating the rotatable base and the angle of rotation is monitored. Then the soundness of the horse's tendons and ligaments is determined to be sound if the hoof can be rotated to an angle of 55° without the horse taking it's weight off the rotatable plate.

The invention will now be described in connection with the accompanying drawings wherein like reference numerals have been used to identify like parts.

DESCRIPTION OF THE DRAWINGS

FIG. 4 is a top or plan view of the apparatus in accordance with a preferred embodiment of the present invention;

FIG. 5 is a side elevational view of the apparatus shown in FIG. 4; and

DESCRIPTION OF THE PREFERRED EMBODIMENTS OF THE INVENTION

Figure 1:
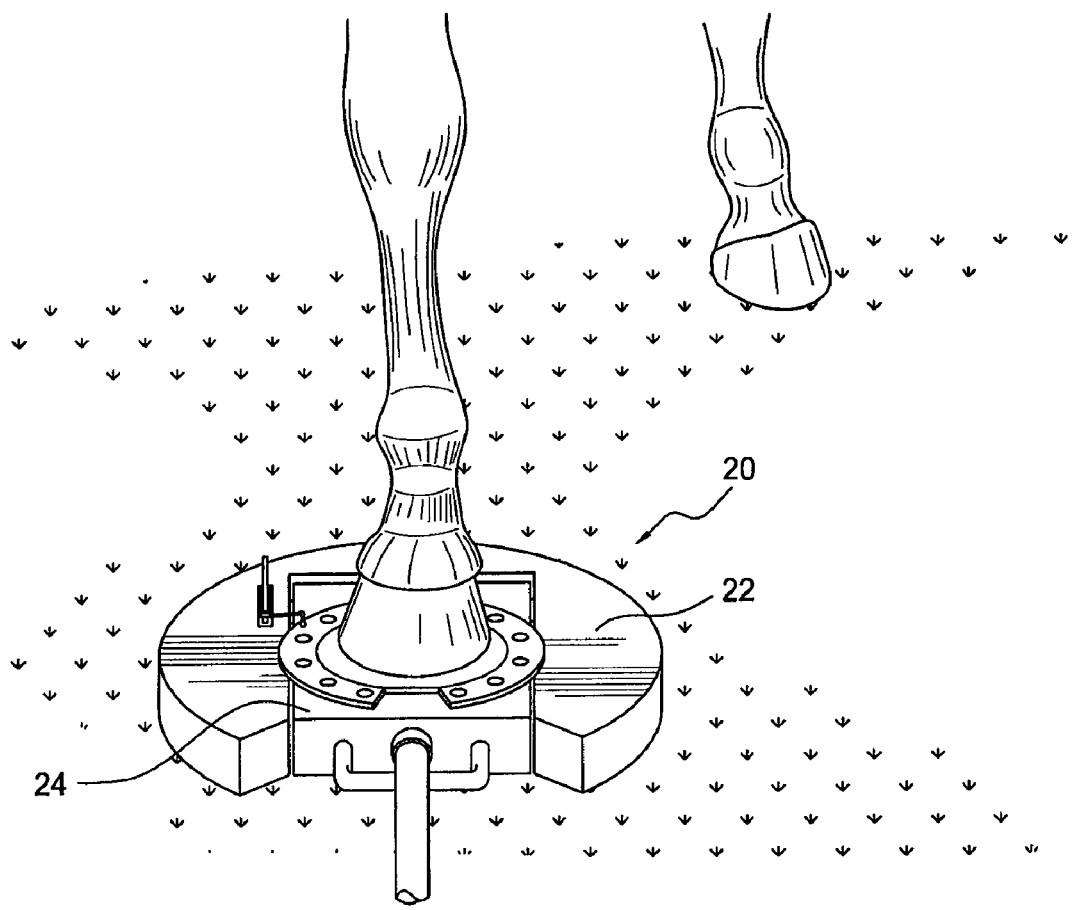
FIG. 1 is a perspective view of an apparatus in accordance with the present invention with a horse's hoof on the apparatus and the rotatable plate in a horizontal position.
Figure 2:
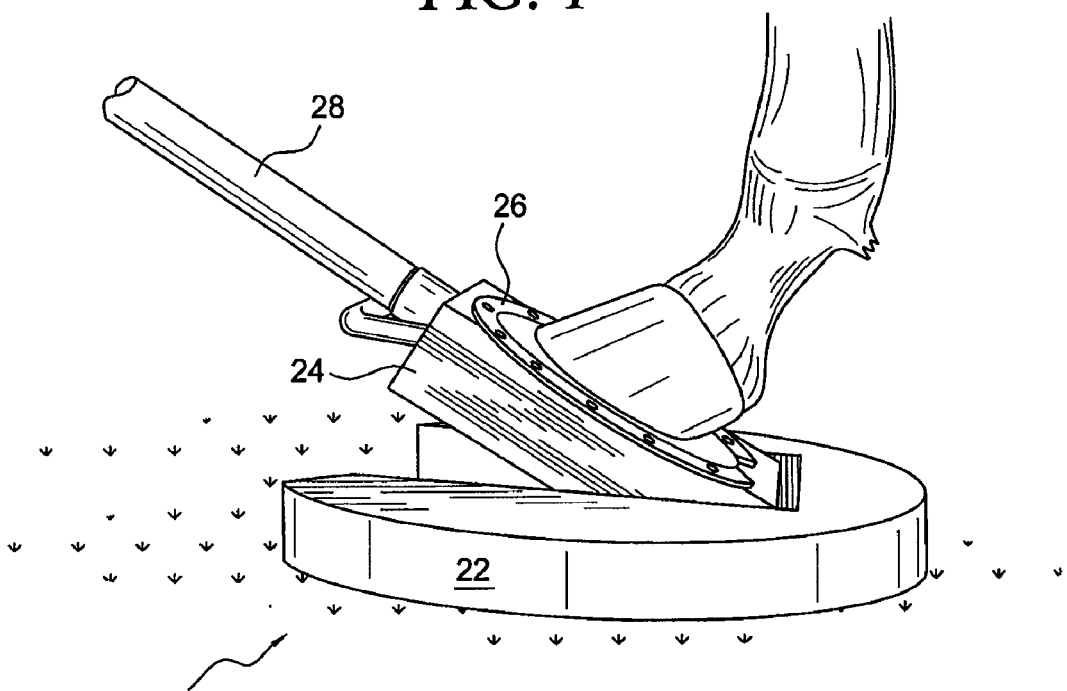
FIG. 2 is perspective view of the apparatus shown in FIG. 1 but with the rotatable plate rotated with the horse's hoof thereon.
Figure 3:
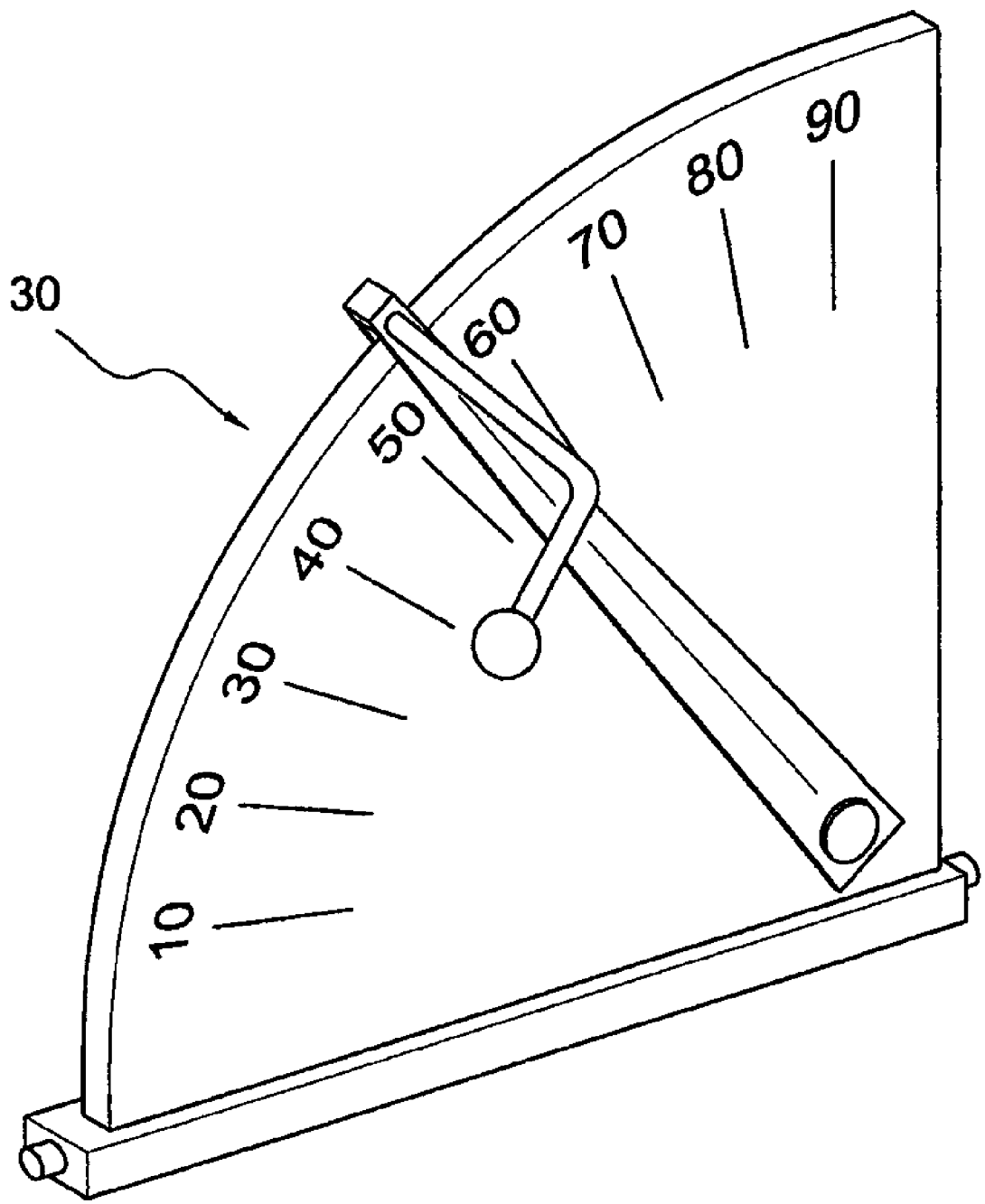
FIG. 3 is a side elevational view of an arc shaped scale as used in the apparatus of the present invention.

As shown in FIGS. 1-5, an apparatus 20 or device for testing a horse's tendons and ligaments include a base plate 22 for positioning on the ground underneath a horse with one leg directly over the apparatus 20. The apparatus 20 is made of iron, steel or preferable an aluminum alloy or other suitable material and includes a rotatable plate 24 pivotally connected to the base plate 22 by a pivot along an axis 25. The rotatable plate 20 also includes a generally horseshoe guide 26 on an upper surface thereof (See FIG. 4) for properly positioning a horse's hoof thereon with a horse standing and it's weight distributed on it's four legs.

A lever or lifting rod 28 is threaded into a rear portion of the rotatable plate 24 i.e. at an opposite side from the pivot or axis 25. The lever or lifting rod 28 is provided for rotating the rotatable plate 24. As shown in FIG. 4, the rod 28 is threaded into the plate 24 and can be removed there from for transportation or storage as a compact device. The rod 28 may also include a second section 29 threaded into one end of the rod 28 to apply more leverage while being removable there from for more compact storage. As shown more clearly in FIG. 5, the rod 28 and section 29 are preferable made of hollow tubes in order to reduce the weight of the apparatus.

An important feature of the apparatus 20 resides in an arcuate scale 30 consisting essentially of a segment of a circle (about ¼ of the circle) with angular indications of zero to 55° as an indication of the angle between the base plate 22 and rotable plate 24. As shown in FIG. 4, the scale 30 is rotatable about an axis that is perpendicular to the axis of rotation of the rotatable plate 24. The scale can then be rotated into a recessed portion of the base plate 22. It is also contemplated the scale or indicator and a pointer 31 may be offset from horizontal so that the rotation of the pointer and the indicated angle are not obstructed by the rotatable plate 24. It is also contemplated that other means such as an audio indicator may be provided to indicate that the rotatable plate has been rotated to an angle of 55°. In this way an individual will know that the tendon and ligaments of the horse's lower leg are sound and that there is no need for further rotation.

Figure 6:
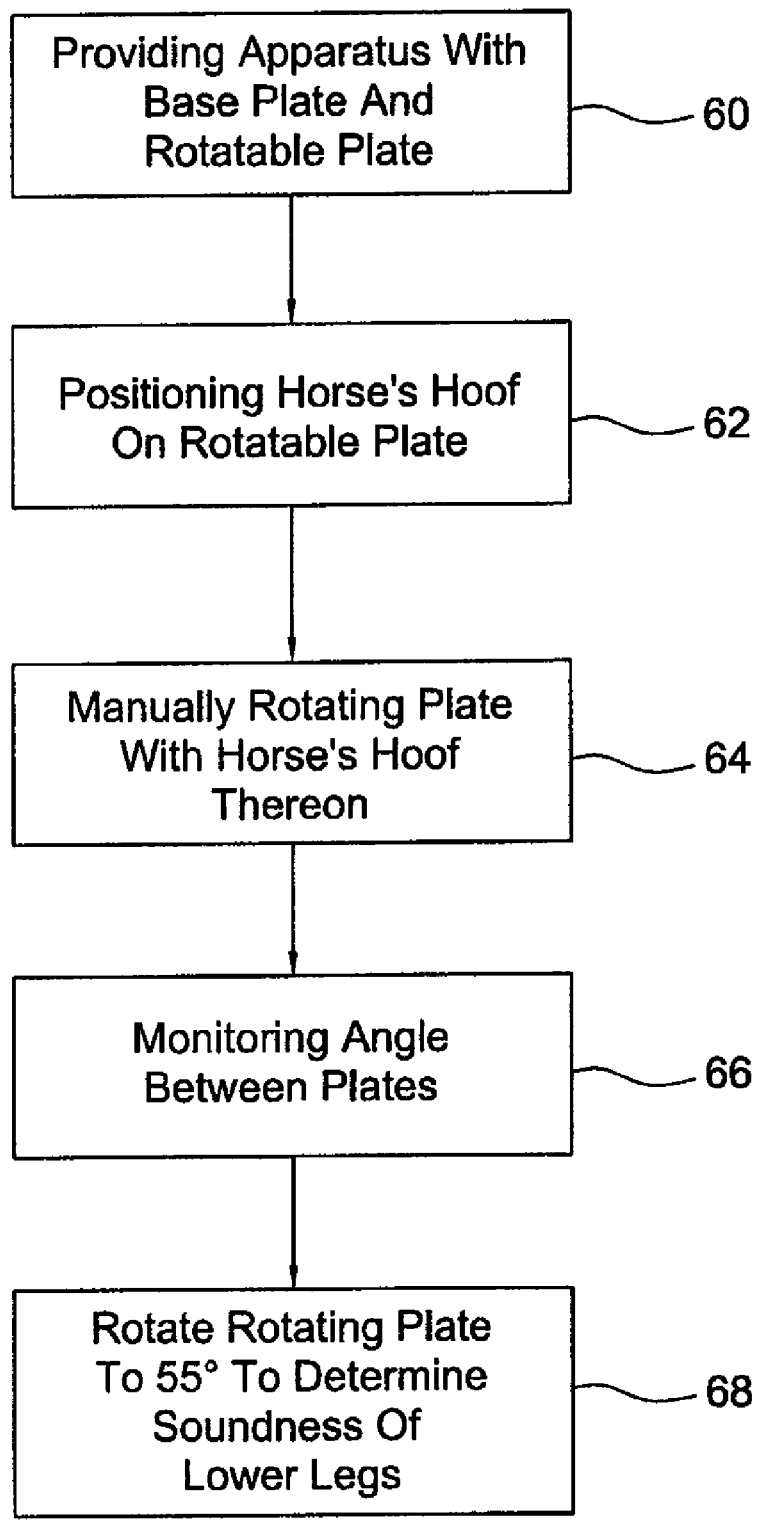
FIG. 6 is a block diagram illustrating a method in accordance with the invention.

A method for testing the soundness of a horse's tendons and ligaments in accordance with a preferred embodiment of the present invention will now be described with reference to FIG. 6. The method is based on the flexion of a horse's lower leg and the use of an apparatus for flexing the leg. To be more specific, the method includes the step 60 of providing an apparatus with a base plate and a rotatable plate that is rotatable with respect to the base plate through an angle of up to 55°. In the preferred embodiment of the invention the rotatable plate includes a generally horseshoe shaped member or element that is adapted to receive a horse's hoof including a horseshoe thereon and position or guide the horse into a standing position with it's weight distributed on it's four legs. The apparatus provided preferably includes the elements set forth with respect to FIGS. 1-5.

In the practice of the method in accordance with a preferred embodiment of the invention, a horse is positioned to stand over the apparatus with one hoof in or on the generally horseshoe member in step 62. The horseshoe shaped member may be slightly raised with a recessed portion where it tends to place a slight grip on the shoe.

In step 64 the horse's lower leg is flexed by manually rotating the rotatable member through an angle of up to 55°. The rotation is accomplished by slowly lifting a lever arm and monitoring the angle between the plates in step 66. Instep 68, the soundness of the lower leg is determined if the rotation of the rotatable plate reaches an angle of 55° without the horse taking its weight off of that leg.

While the invention has been described in connection with its preferred embodiments it should be recognized that changes and modifications may be made therein without departing from the scope of the appended claims.

What is claimed is:

1. An apparatus for testing the soundness of a horse's tendon and ligaments by flexing a horse's lower leg, said apparatus comprising:
    a base plate having a forward and rear portion and adapted to be positioned on the ground beneath a horse's hoof;
    a rotatable plate rotatably fixed to said base plate and rotatable through an angle of at least 55° with respect to said base plate;
    a horseshoe shaped guide means for receiving and positioning the horse's hoof on said rotatable plate with a forward portion of the horse's hoof positioned by said horseshoe shaped guide means on said rotatable plate;
    a lever fixed to a rear portion of said rotatable plate for manually tilting said rotatable plate with the horse's hoof thereon and to rotate the rotatable plate through an angle of 55°; and
    a scale for indicating the angle between said rotatable plate and said base plate as an indication of the soundness of the horse's tendons and ligaments in the horse's lower leg.

2. An apparatus for testing the soundness of a horse's tendons and ligaments according to claim 1 which includes means for anchoring said base plate to the ground.

3. An apparatus for testing the soundness of a horse's tendons and ligaments according to claim 2 in which said means for anchoring said base plate to the ground includes a plurality of holes in said base plate and a plurality of spikes to drive through said holes and into the ground for holding said base plate in a fixed position.

4. An apparatus for testing the soundness of a horse's tendons and ligaments according to claim 1 in which said lever is threadedly received in the rear portion of said rotatable plate.

5. An apparatus for testing the soundness of a horse's tendons and ligaments according to claim 3 in which said lever includes two lengths screwed together for more leverage and unscrewed for storage or transportation.

6. An apparatus for testing the soundness of a horse's tendons and ligaments according to claim 1 in which said scale is arc shaped and positioned in a perpendicular position to said base plate.

7. An apparatus for testing the soundness of a horse's tendons and ligaments according to claim 6 in which said arc shaped scale is rotatably fixed to said base plate and rotatable between a retracted position which is parallel with said base plate and a second position that is perpendicular to said base plate.

8. An apparatus for testing the soundness of a horse's tendons and ligaments by flexing a horse's lower leg, said apparatus comprising:
    a base plate having a forward and rear portion and adapted to be positioned on the ground beneath a horse's hoof and a plurality of holes in said base plate and a plurality of spikes for passing through said holes to anchor said base plate in the ground;
    a rotatable plate having a longitudinal axis rotatably fixed to said forward portion of said base plate and rotatable through an angle of 55° with respect to said base plate on an axis that is perpendicular to said longitudinal axis of said base plate;
    horseshoe shaped guide means for receiving and positioning the horse's hoof on said rotatable plate with a forward portion of the hoof positioned by said horseshoe shaped guide means and with a longitudinal axis of the horse parallel to the longitudinal axis of the rotatable plate;
    a removable lever thredly fixed to a rear portion of said rotatable plate to manually tilt said rotatable plate with the horse's hoof thereon through an angle of 55° and wherein said removable lever includes two lengths screwed together for more leverage and unscrewed for storage; and
    a rotatable arc shaped scale for indicating the angle between said rotatable plate and said base plate as an indication of the soundness of the horse's tendons and ligaments in the lower leg and wherein said arc shaped scale is rotatably fixed to said base plate and rotatable between a retracted position that is generally parallel to said base plate and recessed in said base plate and an erect position that is generally perpendicular to said base plate.

9. An apparatus for testing the soundness of a horse's tendons and ligaments by flexing a horse's lower leg according to claim 8 in which said base plate and said rotatable plate are made of an aluminum alloy and said removable lever includes two hollow sections.

10. An apparatus for testing the soundness of a horse's tendons and ligaments according to claim 9 in which said arc shaped scale is rotatable between a vertical position and a recessed position with said base plate along an axis that is perpendicular to the axis of rotation of said rotatable plate.

11. A method for testing the soundness of a horse's tendons and ligaments by flexing a horse's lower leg, include the steps of:

a.) providing an apparatus with a base plate and a rotatable plate adapted to be rotated with respect to the base plate through an angle of 55°;

b.) positioning a horse's hoof on the rotatable plate with the horse standing in a balanced position on four legs;

c.) elevating the hoof by rotating the rotatable base;

d.) monitoring the angle between the base plate and the rotatable plate;

e.) determining that the horse's tendons and ligaments in the lower leg are sound when an angle of 55° is obtained without the horse taking its weight off of the rotatable plate.

12. A method for testing the soundness of a horse's tendons and ligaments by flexing a horse's lower leg according to claim 11 in which:

the apparatus provided in step a.) includes a plurality of holes in the base plate and a plurality of spikes for anchoring the base plate in the ground and wherein the base plate is anchored in the ground and wherein the rotatable plate includes an horseshoe shaped member having a longitudinal axis for positioning a horse with the horse's longitudinal axis parallel to the longitudinal axis of the horseshoe member, and a lever for manually rotating the rotatable plate and in which the rotatable plate is manually rotated up to an angle of 55°.

* * * * *